(12) United States Patent
Osypka

(10) Patent No.: US 6,978,185 B2
(45) Date of Patent: Dec. 20, 2005

(54) MULTIFILAR CONDUCTOR FOR CARDIAC LEADS

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 390 days.

(21) Appl. No.: 10/192,043

(22) Filed: Jul. 10, 2002

(65) Prior Publication Data

US 2003/0092303 A1    May 15, 2003

Related U.S. Application Data

(60) Provisional application No. 60/346,098, filed on Nov. 9, 2001.

(51) Int. Cl.$^7$ .................................................. A61N 1/05
(52) U.S. Cl. ....................................... 607/122; 607/123
(58) Field of Search .......................... 607/116, 119, 122, 607/123

(56) References Cited

U.S. PATENT DOCUMENTS

| | | |
|---|---|---|
| 3,976,082 A | 8/1976 | Schmitt |
| 4,352,360 A | 10/1982 | King |
| 4,402,330 A * | 9/1983 | Lindemans ................. 607/122 |
| 4,567,900 A | 2/1986 | Moore |
| 4,640,983 A * | 2/1987 | Comte .................... 174/119 R |
| 4,641,656 A | 2/1987 | Smits |
| 4,662,377 A | 5/1987 | Heilman et al. |
| 4,662,382 A | 5/1987 | Sluetz et al. |
| 4,711,251 A | 12/1987 | Stokes |
| 4,774,952 A | 10/1988 | Smits |
| 4,784,161 A | 11/1988 | Skalsky et al. |
| 4,796,643 A | 1/1989 | Nakazawa et al. |
| 4,819,662 A | 4/1989 | Heil, Jr. et al. |
| 4,840,186 A * | 6/1989 | Lekholm et al. ............ 607/116 |
| 4,844,099 A | 7/1989 | Skalsky et al. |
| 4,860,769 A | 8/1989 | Fogarty et al. |
| 4,917,106 A | 4/1990 | Olivier |
| 4,945,922 A | 8/1990 | van Krieken |
| 4,957,118 A | 9/1990 | Erlebacher |
| 4,972,848 A | 11/1990 | Di Domenico et al. |
| 4,974,588 A | 12/1990 | Smits |
| 5,002,067 A | 3/1991 | Berthelsen et al. |
| 5,007,436 A | 4/1991 | Smits |
| 5,076,285 A | 12/1991 | Hess et al. |
| 5,095,916 A | 3/1992 | Smits |
| 5,133,365 A | 7/1992 | Heil, Jr. et al. |
| 5,209,229 A | 5/1993 | Gilli |
| 5,231,996 A | 8/1993 | Bardy et al. |
| 5,255,693 A | 10/1993 | Dutcher et al. |
| 5,257,634 A | 11/1993 | Kroll |
| 5,259,395 A | 11/1993 | Li |
| 5,261,417 A | 11/1993 | Osypka |
| 5,265,623 A | 11/1993 | Kroll et al. |
| 5,282,845 A | 2/1994 | Bush et al. |

(Continued)

FOREIGN PATENT DOCUMENTS

DE            3043189 A1     6/1982

(Continued)

*Primary Examiner*—Kennedy Schaetzle
(74) *Attorney, Agent, or Firm*—Scott D. Wofsy; Edwards & Angell, LLP

(57) ABSTRACT

A permanent implantable lead having an elongated lead body with at least one multifilar conductor having electrically active elements for providing electrical communication between connectors at a proximal end and electrical components at a distal end of the lead body, and one or more electrically inactive elements for insulating the electrically active elements from one another.

15 Claims, 6 Drawing Sheets

U.S. PATENT DOCUMENTS

| | | |
|---|---|---|
| 5,300,107 A | 4/1994 | Stokes et al. |
| 5,342,414 A | 8/1994 | Mehra |
| 5,358,516 A * | 10/1994 | Myers et al. ............... 607/116 |
| 5,411,527 A | 5/1995 | Alt |
| 5,411,544 A | 5/1995 | Mar et al. |
| 5,411,546 A | 5/1995 | Bowald et al. |
| 5,439,485 A | 8/1995 | Mar et al. |
| 5,454,839 A | 10/1995 | Anderson et al. |
| 5,456,706 A | 10/1995 | Pless et al. |
| 5,530,251 A * | 6/1996 | Petric ................... 250/396 ML |
| 5,530,520 A * | 6/1996 | Clearwater ................... 399/366 |
| 5,531,779 A | 7/1996 | Dahl et al. |
| 5,534,022 A | 7/1996 | Hoffmann et al. |
| 5,542,173 A | 8/1996 | Mar et al. |
| 5,571,157 A | 11/1996 | McConnell |
| 5,575,814 A | 11/1996 | Giele et al. |
| 5,591,142 A * | 1/1997 | Van Erp ..................... 604/526 |
| 5,649,967 A * | 7/1997 | De Bellis et al. ............... 607/9 |
| 5,649,974 A | 7/1997 | Nelson et al. |
| 5,662,698 A | 9/1997 | Altman et al. |
| 5,676,694 A | 10/1997 | Boser et al. ................ 607/122 |
| 5,713,944 A | 2/1998 | Kroll |
| 5,772,693 A | 6/1998 | Brownlee |
| 5,796,044 A | 8/1998 | Cobian et al. .............. 174/103 |
| 5,824,029 A | 10/1998 | Weijand et al. ............. 607/122 |
| 5,931,862 A | 8/1999 | Carson |
| 5,957,967 A | 9/1999 | Laske |
| 5,964,795 A | 10/1999 | McVenes et al. |
| 6,006,139 A | 12/1999 | Kruse et al. |
| 6,018,683 A | 1/2000 | Verness et al. |
| 6,029,091 A | 2/2000 | de la Rama et al. |
| 6,038,483 A | 3/2000 | KenKnight et al. |
| 6,050,992 A | 4/2000 | Nichols |
| 6,052,625 A | 4/2000 | Marshall |
| 6,066,166 A | 5/2000 | Bischoff et al. |
| 6,067,471 A | 5/2000 | Warren |
| 6,104,961 A | 8/2000 | Conger et al. |
| 6,119,042 A | 9/2000 | Verness et al. |
| 6,152,954 A | 11/2000 | Scheiner et al. |
| 6,152,955 A | 11/2000 | KenKnight et al. |
| 6,185,464 B1 | 2/2001 | Bonner et al. |
| 6,256,542 B1 | 7/2001 | Marshall et al. |
| 6,295,476 B1 | 9/2001 | Schaenzer ................... 607/122 |
| 2002/0183822 A1 * | 12/2002 | Bodner ....................... 607/122 |

FOREIGN PATENT DOCUMENTS

| | | |
|---|---|---|
| DE | 3046667 A1 | 7/1982 |
| EP | 0414234 A2 | 2/1991 |
| EP | 0491979 A1 | 7/1992 |
| EP | 0692221 B1 | 1/1996 |

* cited by examiner

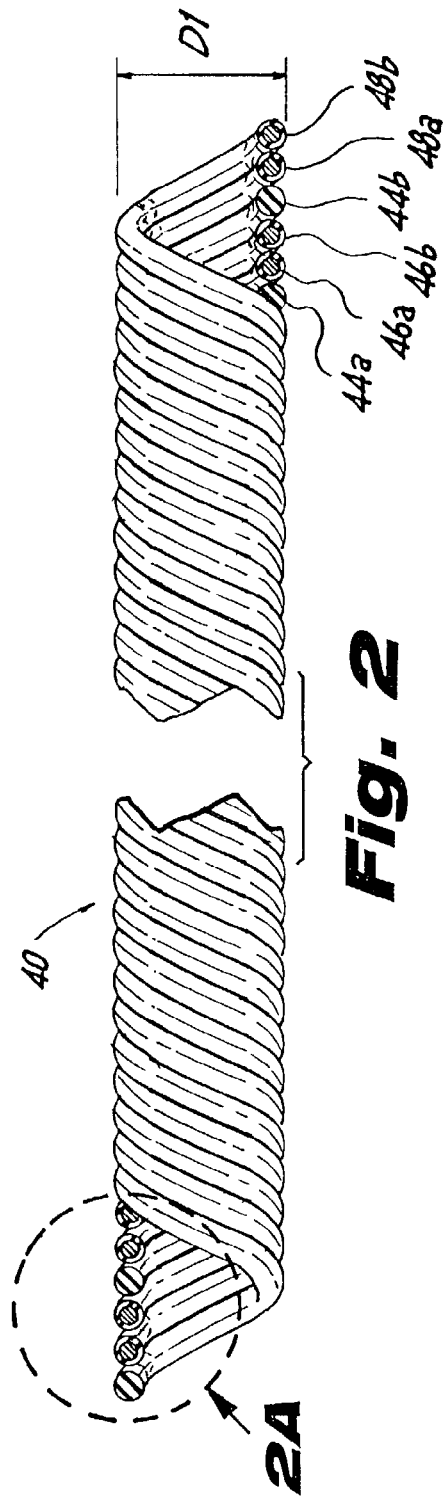
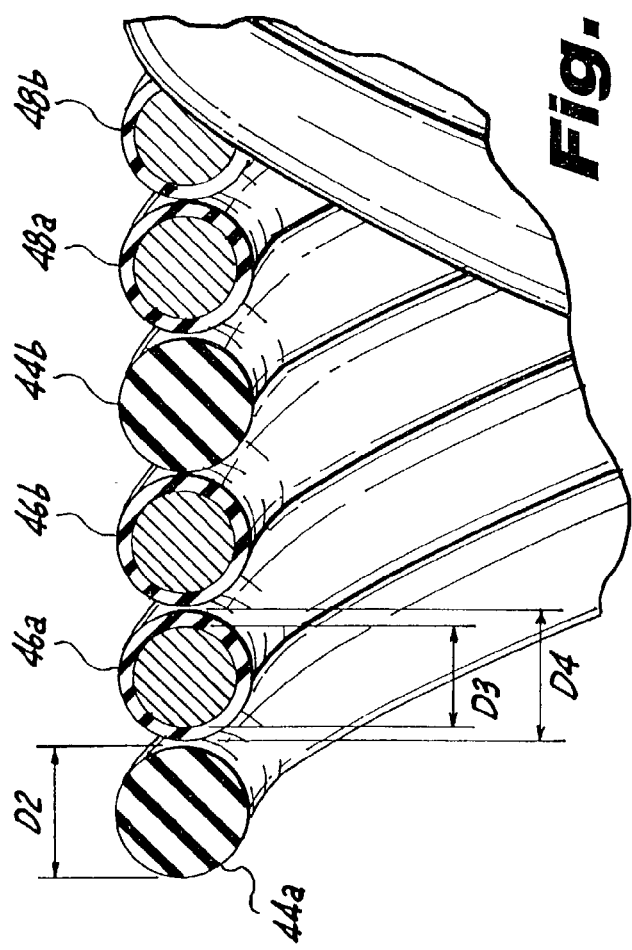

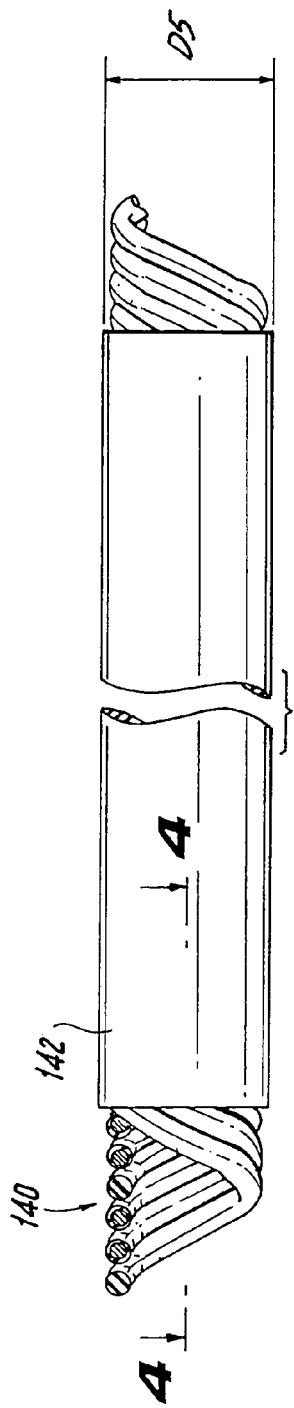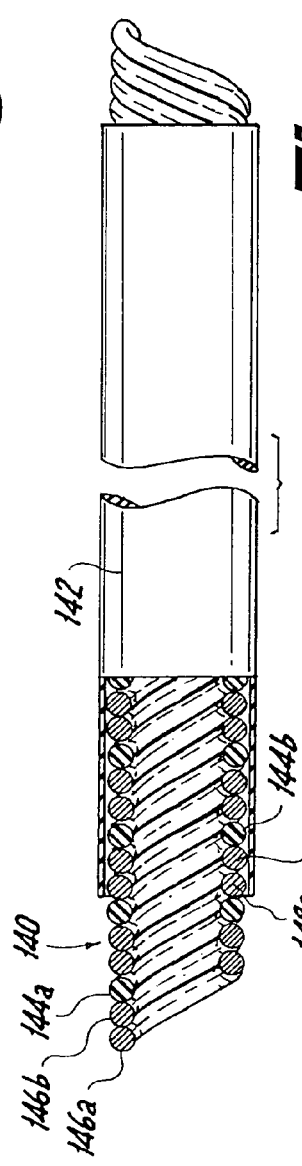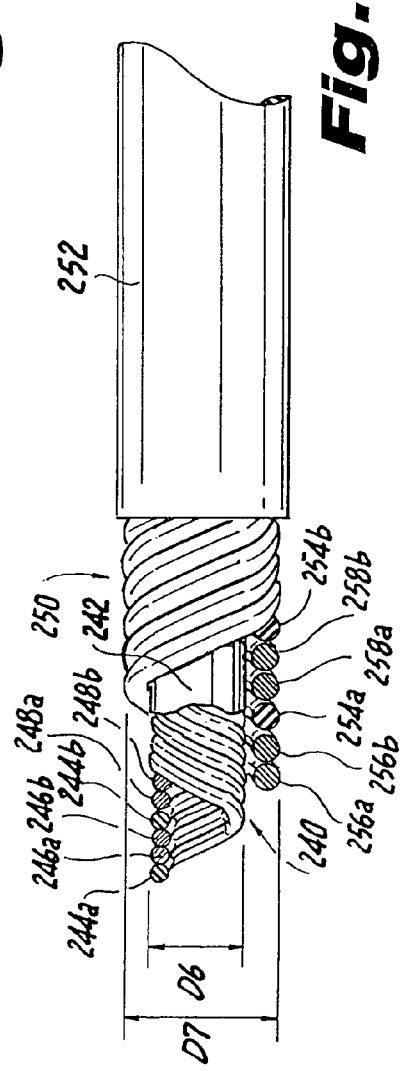

MULTIFILAR CONDUCTOR FOR CARDIAC LEADS

CROSS-REFERENCE TO RELATED APPLICATION(S)

The subject application claims the benefit of commonly owned, copending U.S. Provisional Application Ser. No. 60/346,098, filed Nov. 9, 2001, the disclosure of which is herein incorporated by reference.

BACKGROUND OF THE INVENTION

1. Field of the Invention

The present disclosure relates generally to cardiac pacing and defibrillation leads, and more particularly, to a multifilar conductor for cardiac leads.

2. Background of the Related Art

It is well known in the field of cardiology that certain types of cardiac arrhythmia can be effectively treated by the application of electrical energy to cardiac tissue in an attempt to restore a normal sinus rhythm. Endocardial leads implanted within the heart have been developed to monitor the cardiac state and automatically deliver electrical energy to cardiac tissue. These leads sense the intrinsic rhythm, atrial and ventricular tachycardia and atrial and ventricular fibrillation/flutter.

As used herein, the term ventricular tachycardia refers to any abnormally rapid heart rate (120–180 beats per minute) originating in the ventricles which is generally regular in periodicity and oftentimes is life threatening to the patient. Ventricular fibrillation/flutter is generally a more rapid heartbeat disorder, disorganized and irregular, or non-periodic, and is fatal unless corrected within minutes. Atrial tachycardia and fibrillation/flutter refers to similar abnormal behavior in the atria.

Cardioversion refers to the discharge of electrical energy into the cardiac tissue which may range from a high (40 Joules or more) to a low (less than 1 Joule) energy discharge, but is usually used to describe low energy discharges, typically delivered in the atrium, in an attempt to terminate or revert a tachycardia. Defibrillation usually refers to higher energy electrical discharges, typically delivered to the ventricles, for treating cardiac fibrillation/flutter.

Some leads are designed for defibrillation or pacing but many implantable leads are advantageously fitted for both pacing and defibrillation functions. The typical implantable lead of either arrangement is generally elongated and cylindrical in shape. Thus, for purposes of describing its features, the lead defines two opposing end portions. One end portion (hereinafter referred to as the "distal end"), has various electrodes disposed thereon for sensing heart activity and delivering electrical energy to cardiac tissue. This end is surgically placed adjacent to an inside wall of the heart and is secured at this location either actively with a fixation screw or passively with flexible tines. The other end portion (hereinafter referred to as the "proximal end") is connected by one or more connectors with an implantable device, such as a pacemaker or defibrillator, for monitoring the distal end electrodes and supplying electrical energy.

Under normal conditions, the distal end electrodes are used by the implantable device to monitor the intrinsic electrical activity within the heart. If the implantable device senses abnormal electrical activity, such as that which results from bradycardia, tachycardia or fibrillation, it will respond by directing the appropriate amount of electrical energy to the lead to be discharged by whichever distal end electrodes are necessary to treat the abnormal cardiac activity. Thus, the proper operation of the endocardial lead depends largely on the integrity of electrical communication through the lead.

Multifilar coils constructed of helically-wound electrically conductive elements are currently commonly used to convey electrical current through endocardial leads. The conductive elements, or filars, in the multifilar coil are typically constructed from a conductive low resistance material such as MP35N, Elgiloy® or DFT. The multifilar coil gives the advantage of being highly flexible, yet resistant to breakage. Therefore, it is the current standard practice that all permanent implantable leads use coil conductors, usually having 2, 3 or 4 filars, as conveyers of electrical current through the lead. The distal end electrodes may have singular purpose, such as defibrillators or sensors, or the electrodes may have dual functions, such as pacing/sensing or sensing/defibrillation. Depending on the arrangement and amount of electrodes, the leads may have poles requiring one or more sets of anodes and cathodes. However, defibrillation and pacing functions are not usually combined in one electrode. Pacing involves low voltage discharges which have maximum effect when discharged from small surface areas. Defibrillation involves high voltage discharges which are best delivered by electrodes having larger surface areas to avoid possible tissue damage at the electrode interface and higher impedance at the area of discharge.

Current endocardial leads employ various methods for supplying the necessary electricity to the distal end electrodes. One design incorporates two coil conductors of differing diameter arranged coaxially within the lead body to provide the necessary number of electrodes for the components at the distal end. Although the coaxial arrangement may provide enough electricity for multiple components at the distal end, the configuration also possesses considerable disadvantages. For example, to provide electrical integrity between the coils, the inner and outer coil must be insulated relative to one another by an additional nonconductive covering. If the covering is compromised, which is especially possible for long-term lead implantation, electrical communication between vital components will be compromised. Also, the coaxial design increases the diameter of the lead, which may ultimately render potential applications risky or make incorporating all the desired components impossible.

Another lead design currently used incorporates multiple lumens wherein one or more lumens contain coil conductors while another one or more lumens contain low resistance stranded cable. Typically, the coil conductors connect with pacing electrodes while the stranded cables connect with defibrillation electrodes. Although this configuration reduces the potential for electrical crossover between conductors, it increases the space needed for implantation of the lead and incorporates the inherently less reliable stranded cable which may break due to fatigue or movement of the lead.

A single axis coated wire design has also been used to accommodate the need for multiple components at the distal end. In this design, each filar in a multifilar coil is individually insulated from one another and wound together. Thus, this design can accommodate multiple electrodes with just one multifilar coil without significantly increasing the profile (i.e., diameter) of the lead. However, this configuration also has considerable disadvantages. There is an increased possibility of insulation breakage, especially for long-term lead implantation because the insulation around each individual filar must be extremely thin so that the filars may be wound together. Insulation breakage may result in current leaks and voltage jumps, especially when used for defibrillation. Also, leads with this configuration have a tendency to stretch, which is particularly dangerous if an implanted lead has to be removed.

A general consideration for all leads that incorporate multifilar conductor coils relates to the increase of electrical impedance due to the winding of the filars into a coil configuration. The multifilar coil typically extends through the entire length of the lead body and requires electricity to travel through relatively long wires. The significant increase in the electrical path results in a significant increase in the electrical resistance associated with the wire material. Additionally, since the lead is designed for use with an implantable device, electricity delivered to the lead would be generated via battery power. Therefore, any increase in resistance reduces electrical efficiency and the life of the battery within the implanted device.

It would be advantageous therefore to provide a multifilar conductor coil suitable for incorporation in a single lumen implantable endocardial lead which is reliable and reduces the risk of current leakage, voltage jumps, and loss of electrical integrity. The conductor should neither significantly increase the lead diameter nor stretch during lead implantation and removal. Furthermore, the conductor should minimize the total electrical impedance so as to allow a large current to pass through the lead.

SUMMARY OF THE DISCLOSURE

To provide a solution to the problems and shortcomings associated with prior art endocardial leads, there is disclosed herein a novel multifilar conductor. The novel multifilar conductor disclosed herein includes a plurality of active wires which are insulated from each other by inactive wires. In a lead constructed in accordance with the present disclosure, this configuration, among other things, serves to minimize electrical impedance and the risk of lead body expansion during implantation and removal. Furthermore, a lead constructed in accordance with the present disclosure features a plurality of anodes and cathodes at the distal end without causing an increase in the lead diameter. Most importantly, the multifilar conductor disclosed herein significantly enhances the separation integrity of electrical communication within the lead.

In particular, the present disclosure is directed to an endocardial lead having an elongated lead body with a conductor composed of electrically active elements and one or more electrically inactive elements. The active elements provide electrical communication between the connectors at the proximal end and the electrodes at the distal end of the lead body. The inactive elements insulate the active elements from each other within the lead body. In preferred embodiments, the active and inactive elements are helically-wound together to form the conductor and only the active elements of opposing charges (i.e., positive or negative) are insulated by the inactive elements. Preferably, the conductor has a covering thereon, which may be disposed on and adhered to the conductor and the adjacent lead body via heat-shrinking or otherwise.

In one embodiment of the present disclosure, an implantable endocardial lead having an elongated lead body with opposed proximal and distal end portions is disclosed. There is at least one electrically conductive connector operatively associated with the proximal end portion of the lead body and at least one electrode operatively associated with the distal end portion of the lead body. A conductor extends through the lead body for electrically connecting the at least one connector and the at least one electrode. The conductor is composed of at least first and second electrically active elements and at least one electrically inactive element. The inactive element insulates the first and second electrically active elements from each other.

Preferably, the conductor has a helical configuration and the electrically active elements are electrically conductive wires. Alternatively, the electrically active elements are electrically conductive wires having insulative sheaths. Alternatively, the inactive element is an electrically conductive wire having an insulative sheath. Alternatively, the inactive element is made of a nonconductive material.

In another aspect of the present disclosure, the conductor includes an insulative sheath. Preferably, the insulative sheath is defined by a heat shrinkable polymer tube. The insulative sheath may be constructed of a material such as silicone, polyurethane, a mixture of silicone and polyurethane, polyimide polytetrafloroethylene, or a thermoplastic.

In another aspect of the present disclosure, the lead includes two conductors which extend through the lead body in a coaxial relationship with respect to one another. The two conductors electrically connect the at least one connector and the at least one electrode. Preferably, the two conductors are insulated from each other by a heat shrinkable polymer tube.

In another embodiment of the present disclosure, an implantable endocardial lead having an elongated lead body with opposed proximal and distal end portions is disclosed. At least one electrically conductive connector is operatively associated with the proximal end portion of the lead body and at least one electrode is operatively associated with the distal end portion of the lead body. At least one conductor extends through the lead body for electrically connecting the at least one connector and the at least one electrode. The conductor has at least one first set of electrically active elements, at least one second set of electrically active elements and at least one electrically inactive element. The inactive element is disposed adjacent the at least one first set of electrically active elements and the at least one second set of active elements so as to insulate the at least one first set of electrically active elements from the at least one second set of active elements. Preferably, the first and second sets of electrically active elements each include two or more electrically active elements and the conductor has a helical configuration.

In another embodiment of the present disclosure, at least one coil conductor is electrically connected with a plurality of connectors and a plurality of electrodes. The coil conductor is composed of a plurality of helically-wound electrically active elements and includes a means for minimizing the electrical resistance in the coil conductor. Preferably, the means for minimizing the electrical resistance is at least one electrically nonconductive element that is helically-wound with the plurality of electrically conductive elements of the conductor. Alternatively, the means for minimizing the electrical resistance is at least one electrically inactive element that is helically-wound with the plurality of electrically conductive elements. Both arrangements reduce the operative length of each electrically active element.

These and other unique features of the multifilar conductor of the subject invention will become more readily apparent from the following description of the drawings taken in conjunction with the detailed description of the presently preferred embodiments.

BRIEF DESCRIPTION OF THE DRAWINGS

So that those having ordinary skill in the art to which the present disclosure appertains will more readily understand how to construct and use the multifilar conductor of the subject disclosure, and to illustrate the beneficial and novel features of the subject disclosure, reference may be had to the drawings wherein:

FIG. 2 is a side-elevational view of a preferred embodiment of a multifilar electrical conductor constructed in accordance with the present disclosure;

FIG. 2A is an enlarged localized view of the multifilar conductor coil of FIG. 2, illustrating the relationship between the active and inactive elements thereof;

FIG. 3 is a side-elevational view of another preferred embodiment of a multifilar electrical conductor constructed in accordance with the present disclosure that includes a protective polymer sheath;

FIG. 4 is a cross-sectional view taken along line 4—4 of FIG. 3 illustrating the plurality of elements forming the electrical conductor;

FIG. 5 is a side-elevational view of another embodiment of a multifilar electrical conductor constructed in accordance with the present disclosure having coaxially arranged inner and outer coils each having six elements;

Figure 1:
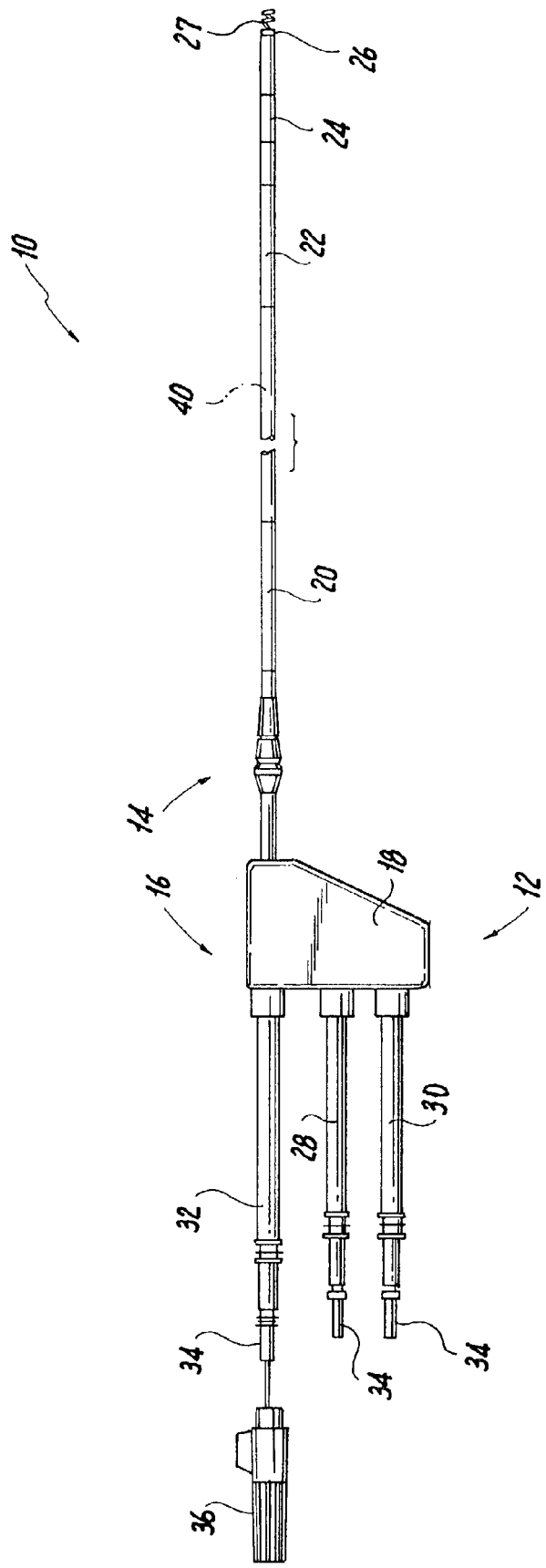
FIG. 1 is a plan view of an endocardial quadripolar defibrillation lead constructed in accordance with a preferred embodiment of the present disclosure.

These and other features of the multifilar conductor of the present disclosure and the endocardial leads incorporating the same will become more readily apparent to those having ordinary skill in the art form the following detailed description of the presently preferred embodiments.

DETAILED DESCRIPTION OF THE DISCLOSURE

In the description which follows the term "proximal" refers to the end of the endocardial lead which is farthest from the surgical site, while the term "distal" refers to the end of the lead which is intended to be closest to the heart. In addition, in the following detailed description of the disclosure, like reference numerals shall be used to identify similar structural elements of the invention disclosed herein.

Referring now to FIG. 1, an endocardial lead fabricated in accordance with the present disclosure is indicated generally by the reference numeral 10. Lead 10 includes an elongated support body or lumen 12 having a distal end portion 14 and a proximal end portion 16. Distal end portion 14 may be straight or have a pre-formed shape, such as a J-shape. Body 12 may include various joints, spacers, extensions and adapters to increase its operational length.

The distal end portion 14 of lead body 12 houses various electrical components used for defibrillation, cardioversion and/or cardiac pacing. The proximal end portion 16 includes a yoke 18 having connectors for electrically linking proximal end portion 16 with an external device (or devices), such as a pacemaker or defibrillator, which controls and supplies power to the electrical components at distal end portion 14. Alternatively, the connectors operatively associated with proximal end portion 16 may be electrically linked with an implantable device, such as an internal pacemaker or defibrillator, for controlling and supplying power to the electrical components at distal end portion 14.

In lead 10, the distal end portion 14 includes electrical components in the form of a first (or "proximal") defibrillation coil 20 for delivering an electrical charge, a second (or "distal") defibrillation coil 22 for delivering an electrical charge, a pacing/sensing ring electrode 24, and a distal tip electrode 26 for pacing/sensing. Ring electrode 24 and tip electrode 26 provide pacing/sensing in different portions of the heart. A helical fixation screw 27 is located at the distal end portion 14 of the lead body 12 for actively securing the device at a desired location. Preferably, helical fixation screw 27 is extendable and retractable through manipulation of a driver 36 associated with proximal end portion 16. It is envisioned that fixation screw 27 is steroid-eluting in that it includes a biocompatible releasing agent contained therein or coated thereon which hastens recovery of the surrounding tissue after screw 27 is secured. Alternatively, tines may be used in place of fixation screw 27. Proximal and distal defibrillation coils 20 and 22, are preferably formed from platinum, iridium, or alloys thereof, and preferably coated with a material of low polarization, such as iridium oxide, titanium, tantalum, or alloys thereof. Preferably, all electrically active surfaces are coated with a material of low polarization., which provides for stable and low cardial stimulation thresholds and favorable sensing properties, among other things.

Yoke 18, which is operatively associated with the proximal end portion 16 of lead body 12, supports a first unipolar connector 28, a second unipolar connector 30 and a bipolar connector 32. Unipolar connectors 28 and 30 may be of the type commonly known in the art as a DF-1 Unipolar. Bipolar connector 32 may be of the type commonly known in the art as IS-1 Bipolar. Connectors 28, 30 and 32 are insulated conductors and each has a terminal end pin 34 for engaging with connector ports of another device, such as an implantable pacemaker or defibrillator. It should be understood by those skilled in the art that the connectors may comprise any suitable configuration that corresponds to the connector ports of the implanted device. In this embodiment, unipolar connector 28 is associated with proximal defibrillation coil 20, unipolar connector 30 is associated with distal defibrillation coil 22, and bipolar connector 32 is associated with ring electrode 24 and pacing/sensing electrode 26. Alternatively, all three connectors 28, 30 and 32 may be united into one connector with 3 or 4 connector electrode rings.

Referring now to FIGS. 2 and 2A, a multifilar conductor 40 provides electrical communication between the electrical components associated with the distal end portion 14 and the connectors associated with the proximal end portion 16. Conductor 40 extends longitudinally through the interior lumen of body 12. Preferably, conductor 40 is in the form of a coil conductor composed of a plurality of adjacent helically-wound elements or filars. Thus, conductor 40 has a generally cylindrical profile and circular cross-section along its latitudinal axis.

In the embodiment of FIG. 2, conductor 40 has six helically wound filars, including two electrically inactive elements 44a and 44b, and electrically active elements 46a, 46b and 48a, 48b. Elements 46a, 46b, which shall be collectively referred to hereinafter as "set 46", are adjacently wound in the coil and carry electricity of the same polarity. Likewise, elements 48a, 48b, which shall be collectively referred to hereafter as "set 48", are adjacently wound and carry electricity of the same polarity. Inactive elements 44a and 44b insulate the active elements of differing charges from one another. Thus, elements in set 46 are insulated from elements in set 48 by elements 44a and 44b which are disposed and wound between the active elements.

It is preferable to provide redundancy in the conductor 40 by utilizing more than one element in each set in the lead to lower the resistance and convey current of the same polarity in case there is a break or lapse of current in a particular element. However, sets 46 and 48 may simply include a single active element to carry current of each charge. It should be understood that is within the purview of the present disclosure to use other conductor arrangements and other numbers of active and inactive elements therein. Preferably, and as shown in FIGS. 2 and 2A, the active elements of sets 46 and 48 have an electrically insulative covering 50 to provide further electrical integrity.

The active elements of sets 46 and 48 are connected with the electrical components of the distal end portion 14. The connections may be made via any conventional means such as laser welding or crimping. The elements associated with a positive charge will be connected to pacing ring 24, and although these elements extend through body 12 to the tip electrode 26, only elements associated with a negative charge will be connected to tip electrode 26. Thus, pacing ring 24 defines an anode and tip electrode 26 defines the cathode. In addition, elements associated with a positive charge are connected with one of the defibrillation coils 20 or 22, while the elements associated with a negative charge are connected with the other defibrillation coil.

Inactive elements 44a and 44b provide greater insulation between the oppositely charged electrically active element sets 46 and 48 than prior art leads. This novel arrangement greatly improves the structural integrity and reliability of lead 10, by, among other things, preventing current leakage, voltage jumps and helping to maintain the electrical circuit should covering 50 on an active filar become torn or fractured. Since the inactive elements 44a and 44b are wound with active element sets 46 and 48 in the coil configuration, the number of revolutions of active element sets 46 and 48 required to make conductor 40 extend through body 12 is less than in prior art coil configurations. By minimizing the length of active elements 46 and 48, the distance required for electricity to travel is less. This minimizes the amount of electrical resistance in the conductor. In accordance with the present disclosure, a plurality of inactive elements may be included in the coil solely for the purpose of minimizing the overall electrical resistance of the conductor.

Inactive elements 44a and 44b may be constructed from a nonconductive biocompatible material, such as Teflon®, polyimide, polyamide (Nylon), polyurethane or other similar material. Inactive elements 44a and 44b may be in the form of a wire, strand or band. To maintain the shape of the nonconductive element and the electrically active elements, it may be necessary to include a heating or tempering process during the actual coil-winding manufacturing process. The tempering process could be also used to melt the inactive element between the active elements which would advantageously alter the stiffness, form and shape of the conductor coil. Alternatively, the inactive elements may be formed from the same wires as the active elements having insulative sheaths, but they are not used to carry a charge. Thus, they are electrically inactive.

In an exemplary embodiment of the present disclosure, the diameter D1 of conductor 40 may range from about 0.50 mm to about 2.0 mm, but is preferred to be about 0.850 mm. The diameter D2 of inactive elements 44a and 44b may range from about 0.10 mm to about 0.20 mm, but is preferred to be about 0.160 mm. The diameter D3 for active element sets 46 and 48 may range from about 0.10 mm to about 0.20 mm without covering 50, but is preferred to be about 0.126 mm. The diameter D4 for active element sets 46 and 48 including covering 50 may range from about 0.10 mm to about 0.20 mm, but is preferred to be about 0.160 mm. These dimensions are not limiting and are used merely for illustrating an embodiment of an endocardial lead constructed in accordance with the present disclosure.

Referring to FIGS. 3 and 4, there is illustrated another embodiment of a conductor fabricated in accordance with the present disclosure and designated generally by reference number 140. Conductor 140 differs from conductor 40 in that it includes an insulative/protective sheath 142 defined by a covering, coating or tube disposed on the outer periphery thereof. Preferably, sheath 142 has been treated to enhance its bonding performance. Sheath 142 prevents conductor 140 from expanding in length, gives the distal end portion of the lead body a preformed memory shape, and provides resiliency and torqueability stiffness along the lead body, among other things. Sheath 142 may be made from a polymer, such as polyurethane, a mixture of silicone and polyurethane, polytetrafloroethylene (PTFE) or another thermoplastic material, and may be disposed over conductor 140 by heat shrinking or some other suitable method for adhering the polymer to conductor 140. For example, conductor 140 may be surrounded by a polyurethane tube which is adhered thereto via heat-shrinking. It is envisioned that the covering or tube may be first treated by etching, or otherwise, to further enhance bonding ability.

As shown in FIG. 4, conductor 140 is wound with two sets of active elements 146a, 146b (collectively referred to hereinafter as "set 146"), and 148a, 148b (collectively referred to hereinafter as "set 148"). Inactive elements 144a and 144b insulate the active elements in set 146 from the active elements in set 148. In an exemplary embodiment of the present disclosure depicted in FIGS. 3 and 4, the diameter D5 of conductor 140 with sheath 142 may be within the range of about 0.60 mm to about 1.20 mm, but preferably is about 0.950 mm.

Figure 6:
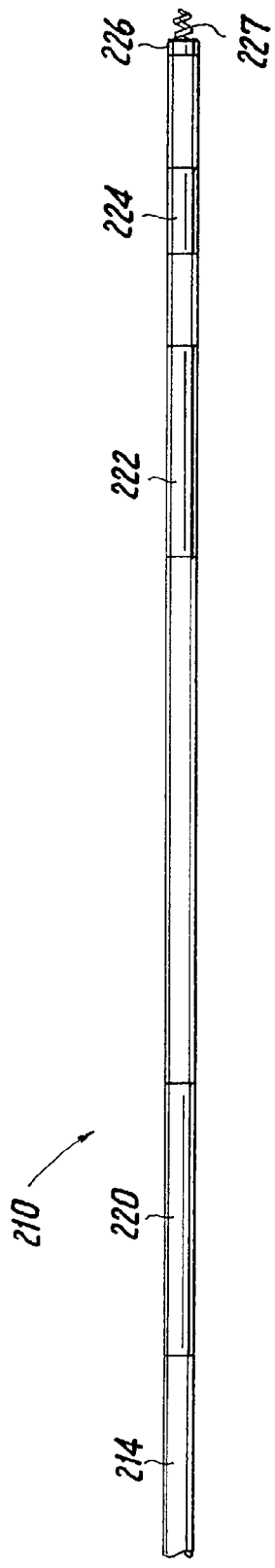
FIG. 6 is a plan view of the distal portion of an endocardial lead which may incorporate the multifilar electrical conductor shown in FIG. 5 or FIG. 4.

FIGS. 5 and 6 depict an exemplary embodiment of an endocardial lead 210 constructed in accordance with the present disclosure. Lead 210 utilizes a coaxial multifilar conductor arrangement having generally concentric conductors. The inner conductor 240 has two sets of dual active elements, 246a, 246b and 248a, 248b, collectively referred to as set 246 and set 248, which are insulated from each other by two inactive elements 244a and 244b. The outer conductor 250 also has two sets of dual active elements, 256a, 256b and 258a, 258b, collectively referred to as set 256 and set 258, which are insulated from each other by two inactive elements 254a and 254b. Both conductors 240 and 250 have insulative sheaths 242 and 252, respectively, for preventing the lengthwise expansion of conductors 240 and 250, giving the distal end portion of the lead body a preformed memory shape, and providing resiliency and torqueability along the lead body, among other things.

For purposes of illustrating the exemplary arrangement in more detail, elements in set 246 of inner conductor 240 and elements in set 256 of outer conductor 250 have been arbitrarily designated as positively charged. Similarly, elements in set 248 of inner conductor and elements in set 258 of outer conductor 250 are designated as negatively charged for purposes of this illustration. Thus, a preferable arrangement would have elements in set 248 connecting with tip electrode 226, elements in set 246 connecting with pacing ring 224, elements in set 256 connecting with distal defibrillation coil 222, and elements in set 258 connecting with proximal defibrillation coil 220.

In an exemplary embodiment of the present disclosure illustrated in FIGS. 5 and 6, inner conductor 240 has a outer diameter D6 which includes a sheath 242 substantially similar to sheath 142 shown in the embodiment of FIGS. 3 and 4. Outer conductor 250 has an outer diameter D7 not including sheath 252. D6 may range from about 0.50 mm to about 1.00 mm, but is preferred to be about 0.950 mm, while D7 may range from about 1.20 mm to about 1.60 mm, but is preferred to be about 1.27 mm. It is preferable that conductors 240 and 250 are suitably sized so that the interior portion of conductor 250 is disposed against, or is partially within, the sheath on conductor 240. This configuration serves to enhance the structural integrity, tensile strength and insulative properties of the lead, among other things.

Figure 7:
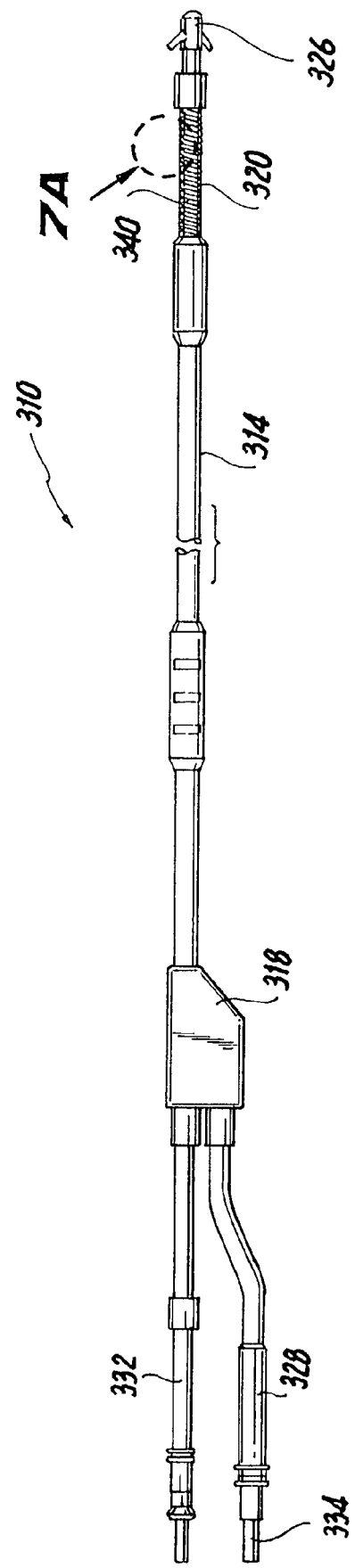
FIG. 7 is a plan view of an endocardial lead constructed in accordance with another embodiment of the present disclosure.
Figure 7A:
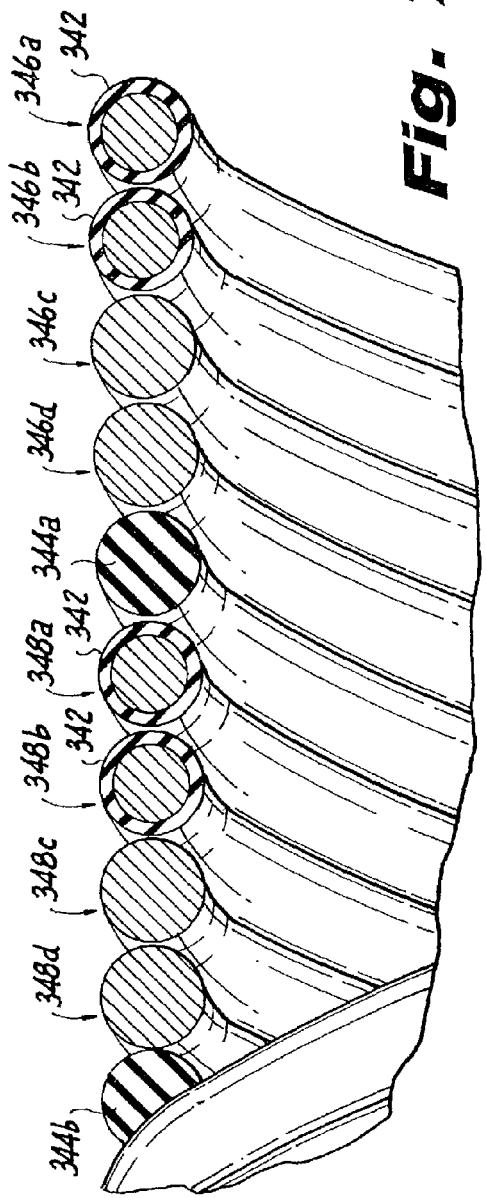
FIG. 7A is an enlarged localized view of the multifilar conductor coil of FIG. 7, illustrating the relationship between the active and inactive elements thereof.

In another embodiment illustrated in FIGS. 7 and 7A, the lead 310 has conductor 340 with two sets of four active elements 346a–d and 348a–d, collectively referred to as set 346 and set 348, which are insulated from each other by two inactive elements 344a and 344b. Conductor 340 has insulative sheaths 342 covering active elements 346a, 346b in set 346 and 348a, 348b in set 348. Active elements 346c, 346d in set 346 and 348c, 348d in set 348 are uncovered. Thus, elements 346c, 346d, 348c and 348d administer defibrillation shocks in area 320 on the distal portion 314 without the need for a separate defibrillation providing apparatus. The remaining two insulated active elements in sets 346 and 348 (i.e., elements 346a, 346b, 348a and 348b), are operatively associated with electrode tip 326 at distal end portion 314.

Figure 8A:
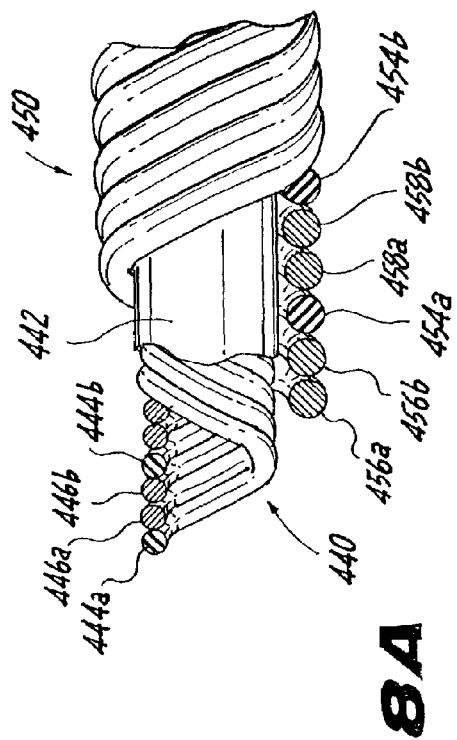
FIG. 8A is an enlarged localized view of the multifilar conductor coil of FIG. 8, illustrating the relationship between the inner and outer conductors and the active and inactive elements thereof.
Figure 8:
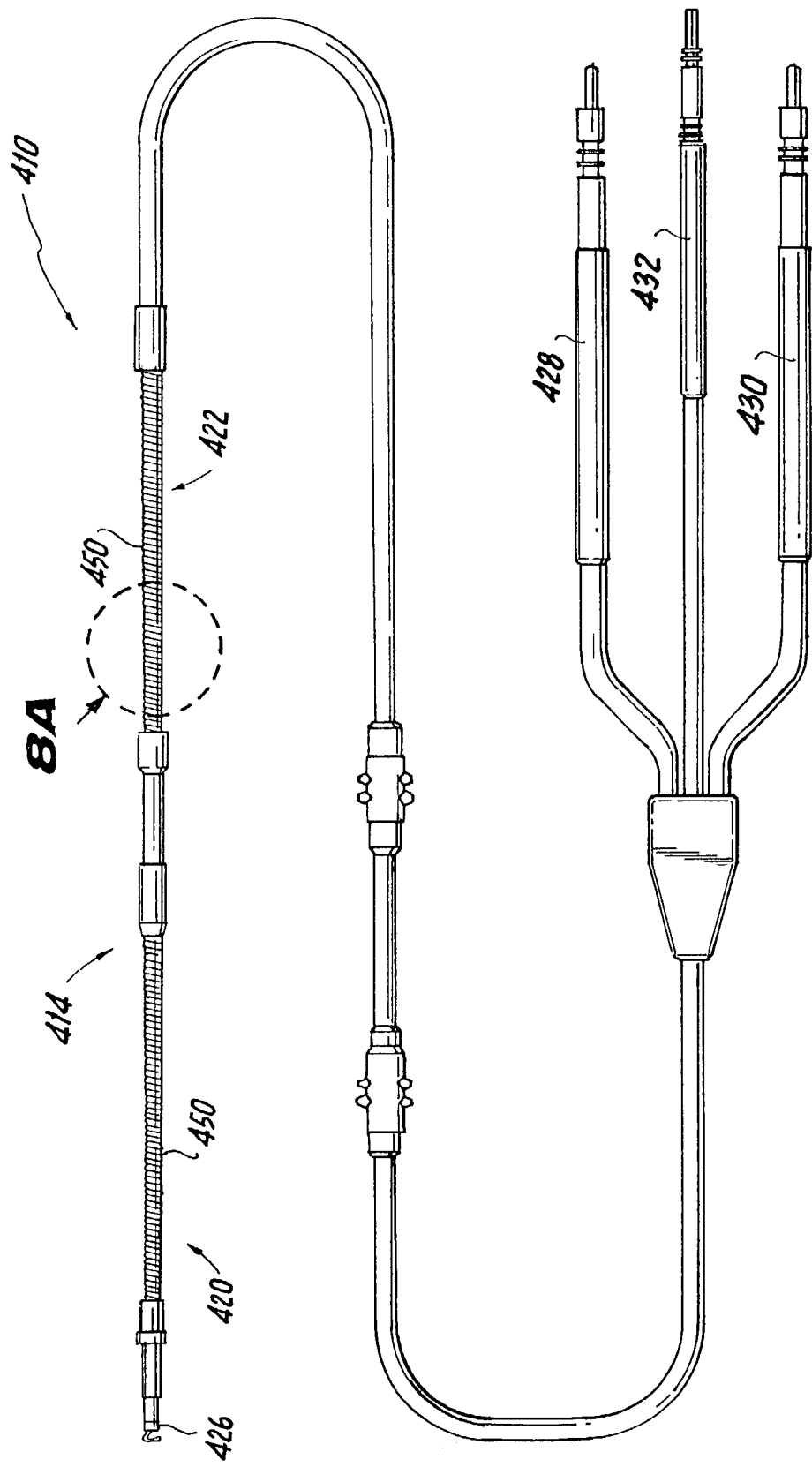
FIG. 8 is a plan view of an endocardial lead constructed in accordance with another embodiment of the present disclosure.

In another embodiment illustrated in FIGS. 8 and 8A, the lead 410 uses a coaxial multifilar conductor arrangement having inner conductor 440 and outer conductor 450. Much like the embodiment illustrated in FIGS. 5 and 6, the inner conductor 440 has two sets of dual active elements 446a, 446b, 448a and 448b, collectively referred to as set 446 and set 448, respectively, which are insulated from each other by two inactive elements 444a and 444b. The outer conductor 450 also has two sets of dual active elements 456a, 456b, 458a and 458b, collectively referred to as set 456 and set 458, respectively, which are insulated from each other by two inactive elements 454a and 454b. Inner conductor 440 has insulative sheath 442 disposed thereon which electrically insulates inner conductor 440 from outer conductor 450. Alternatively, or in combination with sheath 442, the active elements in set 446 and set 448 may be insulated. Defibrillation shocks are administered by active elements in set 456 and set 458 which are exposed in areas 420 and 422 on the distal portion 414 without the need for a separate defibrillation providing apparatus. Inner conductor 440 is operatively associated with electrode tip 426 at distal end portion 414.

Variations of the above-described embodiments of a multifilar conductor according to the present disclosure, using one or more of the features disclosed herein particularly adapted to minimize the electrical resistance and improve upon the electrical integrity of the lead, may of course be used in conjunction with leads having a greater or fewer number of electrodes, connectors and conductors. As such, the above disclosure should be considered exemplary, rather than limiting, with regard to the claims which follow.

What is claimed is:

1. An implantable cardiac lead, comprising:
    a) an elongated lead body having opposed proximal and distal end portions;
    b) at least one electrically conductive connector operatively associated with the proximal end portion of the lead body;
    c) at least one electrode operatively associated with the distal end portion of the lead body; and
    d) a conductor extending through the lead body for electrically connecting the at least one connector and the at least one electrode, the conductor having first and second pairs of adjacently wound electrically active elements and at least one electrically inactive element individually wound between the first and second adjacently wound pairs of electrically active elements and insulating the first and second adjacently wound pairs of electrically active elements from each other, wherein the electrically active elements in each pair of adjacently wound electrically active elements are adapted to convey current of common polarity, and wherein the first and second pairs of adjacently wound electrically active elements and the at least one individually wound electrically inactive element are wound together to form a single helically wound multifilar coil.

2. An implantable cardiac lead as recited in claim 1, wherein the electrically active elements are electrically conductive wires.

3. An implantable cardiac lead as recited in claim 1, wherein the electrically active elements are electrically conductive wires having insulative sheaths.

4. An implantable cardiac lead as recited in claim 1, wherein the conductor includes an insulative sheath.

5. An implantable cardiac lead as recited in claim 4, wherein the insulative sheath is defined by a heat shrinkable polymer tube.

6. An implantable cardiac lead as recited in claim 4, wherein the insulative sheath is constructed of a material selected from the following group consisting of silicone, polyurethane, a mixture of silicone and polyurethane, polytetrafloroethylene, and thermoplastic.

7. An implantable cardiac lead as recited in claim 1, wherein the inactive element is made of a nonconductive material.

8. An implantable cardiac lead as recited in claim 1, wherein two conductors extend through the lead body in a coaxial relationship with respect to one another for electrically connecting the at least one connector and the at least one electrode.

9. An implantable cardiac lead as recited in claim 8, wherein the two conductors are insulated from each other by a heat shrinkable polymer tube.

10. An implantable cardiac lead, comprising:
    a) an elongated lead body having opposed proximal and distal end portions;
    b) at least one electrically conductive connector operatively associated with the proximal end portion of the lead body;

c) at least one electrode operatively associated with the distal end portion of the lead body; and d) at least one conductor extending through the lead body for electrically connecting the at least one connector and the at least one electrode, the at least one conductor having at least one first set of adjacently wound electrically active elements each adapted to convey current of common polarity, at least one second set of adjacently wound electrically active elements each adapted to convey current of common polarity and at least one electrically inactive element disposed adjacent and individually wound together with the at least one first set of adjacently wound electrically active elements and the at least one second set of adjacently wound electrically active elements so as to insulate the at least one first set of adjacently wound electrically active elements from the at least one second set of adjacently wound electrically active elements, and wherein the at least one first set of adjacently wound electrically active elements, the at least one second set of adjacently wound electrically active elements and the at least one individually wound electrically inactive element are wound together in a single helically wound multifilar coil.

11. An implantable cardiac lead as recited in claim 10, wherein the first and second sets of electrically active elements each include two electrically active elements.

12. An implantable cardiac lead as recited in claim 10, wherein at least two conductors extend coaxially through the lead body defining an inner conductor and at least one outer conductor.

13. An implantable cardiac lead as recited in claim 12, further comprising an insulative covering disposed between the inner conductor and at least one outer conductor.

14. An implantable cardiac lead as recited in claim 13, wherein the covering is defined by a heat shrinkable polymer tube.

15. A helically wound multifilar conductor assembly for cardiac leads comprising:

a) a first pair of adjacently wound electrically active filars each adapted to carry current of a first polarity;

b) a second pair of adjacently wound electrically active filars each adapted to carry current of a second polarity; and c) first and second electrically inactive filars individually wound between the first and second pairs of electrically active filars for insulating the first and second pairs of electrically active filars from one another, wherein the first pair of adjacently wound electrically active filars, the second pair of adjacently wound electrically active filars and the first and second individually wound electrically inactive filars are wound together in a single helically wound coil having an outer diameter ranging from about 0.50 mm to about 2.0 mm.

* * * * *